(12) United States Patent
Reaney

(10) Patent No.: US 6,475,758 B2
(45) Date of Patent: Nov. 5, 2002

(54) SOAPSTOCK HYDROLYSIS AND ACIDULATION BY ACIDOGENIC BACTERIA

(75) Inventor: Martin J. T. Reaney, Des Moines, IA (US)

(73) Assignee: Feed Energy Company, Des Moines, IA (US)

( * ) Notice: Subject to any disclaimer, the term of this patent is extended or adjusted under 35 U.S.C. 154(b) by 0 days.

(21) Appl. No.: 09/801,763

(22) Filed: Mar. 9, 2001

(65) Prior Publication Data

US 2002/0009785 A1 Jan. 24, 2002

Related U.S. Application Data

(60) Provisional application No. 60/188,692, filed on Mar. 13, 2000.

(51) Int. Cl.$^7$ .............................. C12N 1/00; C12N 1/12; C12N 1/20; C12P 1/04; C12P 7/64
(52) U.S. Cl. ...................... 435/134; 435/170; 435/243; 435/252.1; 435/252.9; 435/822
(58) Field of Search ............................. 435/243, 252.1, 435/42, 134, 170, 252.9, 822

(56) References Cited

U.S. PATENT DOCUMENTS

| | | | | |
|---|---|---|---|---|
| 2,172,531 A | | 9/1939 | Ekhard ...................... 99/122 |
| 2,899,307 A | | 8/1959 | Wilson ........................ 99/22 |
| 5,518,995 A | * | 5/1996 | Abrams et al. ............. 504/348 |
| 6,060,050 A | * | 5/2000 | Brown et al. ............... 424/93.3 |
| 6,113,908 A | * | 9/2000 | Paton et al. ............. 424/195.1 |
| 6,140,486 A | * | 10/2000 | Facciotti et al. ........... 536/23.2 |
| 6,153,815 A | * | 11/2000 | Covello et al. ............. 800/306 |

OTHER PUBLICATIONS

Steven L. Johanses et al., "Low–molecular weight organic compositions of acid waters from vegetable oil soapstocks." Journal of the American Oil Chemists' Soceity, vol. 73, No. 10, 1996, pp. 1275–1286.

C.W. Hesseltine et al., "Screening of Industrial Microorganisms for growth on soybean soapstock" Process Biochemistry, vol. 22, No. 1, 1987, pp. 9–12.

H. Buchold, "Enzmatische Phosphatidentfernung aus pflanzenoelen" Fett Wissenschaft Technologie– Fat Science Technology, Conradin Industrieverlag, Leinfelden Echterdingen, DE. vol. 95, No. 8, Aug. 1, 1993, pp. 300–304.

\* cited by examiner

*Primary Examiner*—Jean C. Witz
*Assistant Examiner*—Deborah K. Ware
(74) *Attorney, Agent, or Firm*—Dowell & Dowell, P.C.

(57) ABSTRACT

Methods for acidification of soapstock using acids produced by fermentation with acidogenic bacteria and recovery of acidulated fatty acids are disclosed. Soapstock is advantageously acidified by fermentation of endogenous soapstock nutrients and added nutrients under controlled conditions using acidogenic bacteria. The nutrients may include carbohydrate, nitrogen, phosphorous, sulfur from defined or undefined sources. The acidification reaction avoids the use of strong acids for the treatment of soapstock, minimizes wastewater contamination with salts and produces potentially valuable by-products including lactic acid, acetic acid, glyceric acid and nutrient rich microorganisms.

23 Claims, No Drawings

SOAPSTOCK HYDROLYSIS AND ACIDULATION BY ACIDOGENIC BACTERIA

This application claims benefit of priority from Provisional Application Ser. No. 60/188,692 filed Mar. 13, 2000.

BACKGROUND OF THE INVENTION

1. Field of Invention

This invention relates to a process for the separation of fatty acids and oils from soapstock, glyceride oils, phospholipids and mixtures thereof. More particularly the process overcomes the problems of the prior art, which require adding large amounts of mineral acid to hydrolyze the soaps and phospholipids present in the soapstock. Mineral acid addition necessitates the addition of base to neutralize the acidic wastewater generating a high strength salt-water waste stream. The present disclosure reaction is unique in that it allows the utilization of the endogenous nutrients of the soapstock, glycerides and phospholipids plus additional nutrients needed as a feed for the acidogenic microorganisms. The acid generated by the microorganisms is of sufficient strength to allow the recovery of the oil from the soapstock, glycerides and phospholipids. It is an advantage of the current method that the process water is rich in both organic salts and organic acids that may be recovered as a valuable by-product of the current process. It is a further advantage of the current method that the process converts a portion of the nutrients into a microorganism mass that is a concentrated source of nutrients for animal feed or even human consumption. It is a further advantage of this process that polar molecules released by hydrolysis of soapstock, glycerides and phospholipid molecules may be converted to organic acids, salts of organic acids and nutrients for animal feed. This conversion greatly reduces the organic matter that occurs in the soapstock wastewater. It is a further advantage of this process that the soaps act as a buffer controlling pH between 5 and 7 through most of the fermentation process, which allows the organic salts to build to very high concentrations without inhibiting bacterial growth.

2. Description of the Related Art

Crude glyceride oils obtained from seeds, fruits and plants such as soybean and canola oil contain free fatty acids, phospholipids and other impurities. Contacting the crude oil sequentially with acid and then alkali in a batch or continuous process refines such crude oil. The acid treatment reacts with phospholipid materials, (also known as gums or lecithin) and causes them to precipitate. The alkali reacts with the free fatty acids to form soap that may be separated from the oil by settling or centrifugation to yield soapstock. In modern industrial practice gums and soapstock may be prepared separately or combined. Thus the major by-products of refining vegetable oil are crude phospholipids, soapstock, glycerides or mixtures thereof.

From soybean, the predominant source of edible oil in the United States, refining byproducts are generated at a rate of about 6% of the volume of crude oil produced (Anonymous, Soya Bluebook Plus, Soyatech, Inc., Bar Harbor, Me., 1995, p. 262.), amounting to as much as approximately one billion pounds annually. Its price can be as low as one-tenth that of refined vegetable oil. Where possible, recovery of value from by-products is achieved by adding a mineral acid to the byproducts to separate lipids from the water, sodium and other contaminants.

Treatment of refining byproducts with strong mineral acid separates the material into three distinct layers. The upper layer is a material of commerce referred to as acidulated soapstock. The middle layer is an emulsion containing both water and lipid while the lower layer is a strongly acidic wastewater. In commercial practice the water must be neutralized by the addition of caustic prior to disposal in municipal sewers. The result of using first strong acid followed by strong base produces a wastewater that is a heavily concentrated mineral salt solution. Brister (U.S. Pat. No. 4,671,902), for example, treated 75,000 kg soapstock with sulfuric acid to reduce the pH to 3 and separated 28,000 kg of fatty sludge and an unstated amount of water. Brister makes no further mention of the treatment of the acid rich water that is the major product of the treatment of soapstock. Phillips and Leavens (U.S. Pat. No. 4,100,181) and Red and Ilagen (U.S. Pat. No. 4,118,407) recommend acidulation of soap stock with mineral acids such as sulfuric acid and hydrochloric acid to liberate fatty acids from the soap present, separating the resulting acid oil and aqueous saline phases.

Dowd (Journal of the American Oil Chemist's Society Vol. 73 pp.1287–1295) analyzed cottonseed soapstock and found that it contained a series of water-soluble compounds. Johansen et al. (Journal of the American Oil Chemist's Society Vol. 73, pp. 1275–1286) reported between 2.5% and 15% dissolved solids in the acid water of acidulated soapstock. The dissolved solids certainly contained sulfuric acid and sodium sulfate as residual salts from acidulation but many soluble organic compounds including carbohydrates were identified. Johansen et al. (Journal of the American Oil Chemist's Society Vol. 73, pp. 1275–1286) noted the presence of lactic acid in all of the soapstock materials tested and speculated that this fatty acid that this acid arose from fermentation of other carbohydrates present in the soapstock.

Organic acid production is readily achieved by fermentation of nutrient rich materials in the presence of acidogenic bacteria such as bacteria from the genera Bacillus, Lactobacillus or Streptococcus. In our invention we have discovered that acidogenic bacteria can metabolize nutrients to produce organic acids that may be used to split soapstock. During acidification, soapstock buffers the pH of the acid fermentation and prevents acids from lowering production of organic acid. Enzymes including lipases and phospholipases synthesized by the acidogenic bacteria can improve the separation of lipids from these byproducts. Acidogenic bacteria transformed by introduction of appropriate DNA to produce lipases and phospholipases may also be used for this technology.

SUMMARY OF THE INVENTION

By-products of the oilseed processing industry contain lipids, water and water-soluble organic materials. Although these by-products have a relatively low value they may be readily converted into more valuable products by addition of strong mineral acids in a process known as acidulation. The conventional process for acidulation and recovery of lipids from refining byproducts requires the addition of large excesses of acid at high temperatures to recover the fatty acid rich oil.

It is an object of this invention to acidulate and hydrolyze these byproducts with an acidogenic bacteria culture so as to produce sufficient organic acid to substantially split the by-product into two phases while minimizing the production of an interphase. It as an object of this invention to produce high levels of organic acid salts in a lactic acid fermentation by buffering the pH with fatty soaps.

It is a further object of this invention is to recover live bacterial culture from the acid water and split soapstock, crude lecithin or gummed soapstock and add this culture to future batches for splitting. It is a further object of this invention to continuously split soapstock, crude lecithin or gummed soapstock with an acidogenic bacterium in a bioreactor. It is a further object of this invention to utilize both acidogenic bacteria and mineral acid to split soapstock where pH reduction by acidogenic bacteria is not sufficient to effectively split all fatty acids. It is a further object of this invention to produce value added acids such as lactic acid, citric acid, butyric acid, propionic acid and acetic acid by extracting and concentrating the aqueous phase. It is a further object of this invention to recover sodium hydroxide from the sodium lactate present in the wastewater by salt splitting using electrolysis. It is an object of this invention to utilize acidogenic bacteria that produce lipase and phospholipase to enhance the splitting of soapstock into two phases.

By one aspect of this invention there is provided a method for producing a fatty acid rich oil and an aqueous solution containing recoverable organic acids from a byproduct of vegetable oil refining comprising soapstock, glyceride, phospholipid and mixtures thereof, comprising pasteurizing, cooling and fermenting said byproduct material with an acidogenic bacterial culture and nutrients so as to produce sufficient organic acid to acidify said byproduct and recovering said fatty acid rich oil and said aqueous solution from said acidified byproduct.

DESCRIPTION OF THE PREFERRED EMBODIMENT

This invention describes the acidulation of soapstock, phospholipid, glyceride or mixtures thereof with an acidogenic bacteria culture from the genera Bacillus, Lactobacillus, Streptococcus or bacteria from other genera that produce organic acids by incubating with sufficient nutrients for the bacteria to produce acid necessary for acidification. The required culture can be obtained from readily available commercial sources including, but not limited to, sour cream, yoghurt and sauerkraut. In a preferred embodiment soapstock, glyceride, phospholipid or mixture thereof, which may derive from any oilseed stock such as canola, cottonseed, corn, palm, soybean, coconut, flax, rapeseed, mustard, safflower, hempseed or other vegetable oil, is heated to minimize existing bacterial contamination by pasteurization. After heating the soapstock, glyceride, phospholipid or mixture thereof is cooled to a temperature suitable for growth of acidogenic bacteria, preferably in the range of 10–60° C., and more preferably 45–50° C. At this temperature nutrients required for acid production are added and the byproduct is inoculated with a culture of bacteria that are acclimatized to grow rapidly in and produce acid. Nutrients include carbohydrate rich waste materials such as waste bread, restaurant waste and potato processing waste, or carbohydrate rich commercial products such as whey, cornstarch, high fructose corn syrup, potatoes and molasses.

The fermentation is allowed to proceed until the byproduct has been sufficiently acidified to allow separation of the acidulated fatty acids and water. After acidulation bacteria may be isolated from both the oil and water phases by filtration and returned for subsequent inoculation of future batches. The oil phase generated may be used in traditional applications such as animal feeds and as a resource for fatty acid production. The wastewater from acidulation by microbial reaction may be used as a source of organic acids and in a preferred embodiment as a source of lactic acid. In a preferred embodiment organic acids occur in the wastewater primarily as their sodium salts. The sodium lactate is readily converted to sodium hydroxide and lactic acid by known methods such as those disclosed in U.S. Pat. No. 5,002,881 where the wastewater is subjected to ultrafiltration followed by separation of salt and water by bipolar membranes.

In another preferred embodiment a continuous culture of acidogenic bacteria is maintained at constant temperature and pH conditions by feeding nutrients to lower the pH and pasteurized soapstock to raise the pH. In the continuous process acidulated fatty acids and water are removed in order to maintain the reactor at a constant volume.

The byproducts from the vegetable refining of the present invention may include metal soaps. In some embodiments the metal may be a divalent or trivalent metal. By way of example, metals may be selected from a group consisting of sodium, potassium, lithium, calcium, and magnesium.

In addition to the foregoing, the byproducts from the vegetable oil refining may also contain soaps of ammonium or organic bases which are used in the refining of vegetable oils.

As previously noted, the acidogenic bacterial cultures used in the present invention may be genetically modified to produce lipolytic enzymes. Further, the acidogenic bacterial cultures may be selected from strains of bacteria that naturally produce elevated levels of lipolytic enzymes. The lipolytic enzymes may include enzymes from a group consisting of lipase, phospholipase A1, phospholipase A2, phospholipase C and phospholipase D. The lipolytic enzymes are also heat tolerant.

EXAMPLES

Example 1
Separation of Soapstock, Glyceride, and Phospholipid Mixtures using a Culture of *Lactobacillus acidophilus*

Commercial soapstock, comprising a mixture of soapstock, glyceride, and phospholipid, (1000 g; 67% moisture content) was heated to 90° C. for 30 minutes to minimize contamination by endogenous bacteria in a 4 L beaker. The pasteurized mixture was then brought to pH 7.0 by treatment with a small amount of lactic acid and 20 grams of sucrose were added. The mixture was brought to 45° C. in an incubator and a culture of *Lactobacillus acidophilus* was added by the addition of Dannon plain yogurt to initiate the acidification. The culture was maintained 45° C. with gentle stirring approximately every 2–8 hours for 48 hours.

During incubation some gas bubbles were observed in the mixture and the viscosity decreased. The reaction contents separated into two phases during the incubation. The lower phase 680 g was observed to be predominantly water and the upper phase (305 g) was first a mixture of water, soap and oil then finally the upper phase became mostly cloudy oil. Approximately 25 g of material were lost either through evaporation or coated onto glassware. The pH of the upper phase could not be reasonably measured. The pH of the lower phase steadily decreased as acid was produced from metabolism of the sugars generated both from endogenous nutrients, present in the mixture, and the added nutrient sugar. The final pH of the mixture after 48 hours was 5.1. Water content of the acidulated oil produced in this manner was 3.0%.

Example 2
Continuous Acidification of Soapstock, Glyceride, and Phospholipid Mixtures using a Culture of *Lactobacillus acidophilus*.

Commercial soapstock, a mixture of soapstock, glyceride, and phospholipid, (1000 g; 67% moisture content) was prepared and inoculated with bacteria as described in example 1. After 72 hours incubation with bacteria (1% inoculum with commercial yogurt) and carbohydrates (4% sucrose by weight of soapstock) the fermenter contents had split into two phases. The pH of the lower aqueous phase was 4.9. A second pasteurized commercial soapstock (2,000 g moisture content 47%) with a pH of 8.5 was added slowly to the fermenter. The aqueous phase volume of the combined fractions increased immediately after mixing to 1.75 L and the pH of the aqueous phase of the combined soapstock was 6.5. The upper layer of this fermentation was viscous but liquid. Sucrose (80 g) was added to the combined soapstock in the 4 L vessel and the mixture was fermented with stirring for an additional 24 hours. During the next 24 hours the pH of the aqueous layer dropped to 4.7 and the upper phase of the reaction became a thin liquid with little viscosity.

The two layers produced in the second incubation were separated and 700 ml of lower aqueous phase and 300 mL of upper oil phase were added to sterile 4 L beaker and mixed with 2,000 g of pasteurized commercial soapstock (pH 8.5 water content 47%) and 80 g of sucrose. Upon mixing a rapid separation of two phases occurred with 1.61 L of aqueous phase of the combined soapstock of 6.8 and a viscous but liquid upper phase. During the next 24 hours of incubation at 45° C. the pH of the aqueous layer dropped to 5.1 and the upper phase of the reaction became a thin liquid with little viscosity.

A fourth cycle of fermentation was initiated by mixing 300 mL of lower aqueous phase and 700 mL of upper oil phase to a sterile 4 L beaker with 2,000 g of pasteurized commercial soapstock (pH 8.5 water content 47%) and 80 g of sucrose. Results were similar to those for the third incubation step.

It is clear that according to the present method soapstock may be continuously separated by addition of fresh soapstock and removal of low viscosity oil and water.

Example 3
Recovery of Clear Oil From a Soapstock, Glyceride, and Phospholipid Mixture by Combined Fermentation and Acidulation.

Oil recovered from the multiple cycle fermentation contained 18% water on a w/w basis. Acidulated oil would have less than 5% water. It was decided to attempt complete acidulation of oil by combined fermentative acidulation and mineral acid acidulation. Sulfuric acid 5 g was added to 1000 g of upper phase oil collected from the fourth fermentation described in example 2. The reaction mixture was heated to 90° C. then allowed to settle. After settling an upper layer of clear dark oil (800 g) was observed over a creamy aqueous layer (180 mL). The clear dark oil had moisture content of 4.7%.

Example 4
Acidification of a Soapstock, Glyceride, and Phospholipid Mixture with Mineral Acid As a counter example a commercial soapstock was acidified in the traditional manner using sulfuric acid alone. Soapstock (1,000 g pH 8.5 water content 47% water w/w) was mixed with 50 g of sulfuric acid and the combined material was heated to 80° C. for 2 hours. During heating the soapstock separated into 3 phases an upper oil phase (380 g<5% moisture) a lower aqueous phase (510 g 20% solids) and an emulsified phase (140 g). Approximately 20 g of material was lost due to evaporation and contamination of glass surfaces during transfers.

When comparing examples 4 and 3 it is apparent that different amounts of mineral acid are required to isolate fatty acids. In example 4, 50 g of sulfuric acid are required to liberate 380 g of acidulated soapstock while in example 3, 5 g of acid liberated 800 g of acidulated soapstock of the same moisture content. The efficiency of mineral acid use increased 21 fold.

What is claimed is:

1. A method for producing a fatty acid rich oil and organic acids from a byproduct obtained from vegetable oil refining and, said byproduct being selected from a group consisting of soapstocks, glycerides, phospholipids and mixtures thereof, the method comprising the steps of:
   A. initially pasteurizing the byproduct to reduce existing bacteria in the byproduct;
   B. thereafter cooling the byproduct to a temperature for supporting growth of an acidogenic bacteria;
   C. subsequently fermenting the byproduct with an acidogenic bacterial culture and nutrients for promoting acid production so as to produce organic acid to acidify the byproduct and cause separation of a fatty acid rich oil and an aqueous solution containing recoverable organic acids; and
   D. thereafter, recovering the fatty acid rich oil and recovering the organic acids from said aqueous solution.

2. The method according to claim 1, including deriving the byproduct from an oilseed stock selected from a group consisting of canola, cottonseed, corn, palm, soybean, coconut, flax, rapeseed, mustard, safflower, hempseed and other vegetable oils.

3. The method according to claim 1, where the byproduct contains a metal soap.

4. The method according to claim 3 where the metal soap is a divalent or trivalent metal soap.

5. The method according to claim 4 where the metal soap is selected from a group consisting of sodium, potassium, lithium, calcium, and magnesium.

6. The method according to claim 1, where the byproduct contains soaps of ammonia or organic bases used in refining vegetable oil.

7. The method according to claim 1, where the acidogenic bacteria is selected from a genera of a group consisting of Bacillus, Lactobacillus, and Streptococcus.

8. The method according to claim 1, where the fermenting of step C is carried out at a temperature between 10 and 60° C.

9. The method according to claim 8, where the temperature is between 45 and 50° C.

10. The method according to claim 1, where the nutrients of step C are selected from a group consisting of waste bread, restaurant waste, and potato processing waste.

11. The method according to claim 1 where the nutrients of step C are selected from a group consisting of whey, cornstarch, potatoes and molasses.

12. The method according to claim 1, where the fermenting of step C is a continuous process.

13. The method according to claim 1, where the fermenting of step C is a batch process.

14. The method according to claim 1, where the acidogenic bacterial culture has been genetically modified so as to produce a lipolytic enzyme.

15. The method according to claim 1, where the acidogenic bacterial culture is selected from strains of bacteria that produce elevated levels of a lipolytic enzyme.

16. The method according to claim 14, where the lipolytic enzyme is selected from a group consisting of lipase, phospholipase A1, phospholipase A2, phospholipase C and phospholipase D.

17. The method according to claim 15, where the lipolytic enzyme is selected from a group consisting of lipase, phospholipase A1, phospholipase A2, phospholipase C and phospholipase D.

18. The method according to claim 14, where the lipolytic enzyme is heat tolerant.

19. The method according to claim 15, where the lipolytic enzyme is heat tolerant.

20. The method according to claim 14, including recovering the lipolytic enzyme from the fatty acid rich oil and the aqueous solution.

21. The process according to claim 15, including recovering the lipolytic enzyme from the fatty acid rich oil and the aqueous solution.

22. The method of claim 12 including recovering acidogenic bacteria from the fatty acid rich oil and the aqueous solution and returning the recovered acidogenic bacteria for subsequent fermenting.

23. The method of claim 1 including recovering acidogenic bacteria from the fatty acid rich oil and the aqueous solution and returning the recovered acidogenic bacteria for subsequent fermenting.

* * * * *